United States Patent
Lee-Chen et al.

(10) Patent No.: US 9,393,229 B2
(45) Date of Patent: Jul. 19, 2016

(54) METHOD FOR TREATING ABNORMAL POLYGLUTAMINE-MEDIATED DISEASE

(71) Applicant: NATIONAL TAIWAN NORMAL UNIVERSITY, Taipei (TW)

(72) Inventors: Guey-Jen Lee-Chen, Taipei (TW); Hsiu-Mei Hsieh, Taipei (TW); Ching-Fa Yao, Taipei (TW)

(73) Assignee: NATIONAL TAIWAN NORMAL UNIVERSITY (TW)

( * ) Notice: Subject to any disclaimer, the term of this patent is extended or adjusted under 35 U.S.C. 154(b) by 212 days.

(21) Appl. No.: 14/282,366

(22) Filed: May 20, 2014

(65) Prior Publication Data
US 2014/0357689 A1    Dec. 4, 2014

(30) Foreign Application Priority Data

May 31, 2013   (TW) .............................. 102119511 A

(51) Int. Cl.
| | | |
|---|---|---|
| *A61K 31/122* | (2006.01) | |
| *A61K 31/40* | (2006.01) | |
| *A61K 31/403* | (2006.01) | |
| *A61K 31/404* | (2006.01) | |

(52) U.S. Cl.
CPC ............. *A61K 31/404* (2013.01); *A61K 31/122* (2013.01); *A61K 31/40* (2013.01); *A61K 31/403* (2013.01)

(58) Field of Classification Search
CPC ... A61K 31/122; A61K 31/40; A61K 31/403; A61K 31/404
See application file for complete search history.

(56) References Cited

FOREIGN PATENT DOCUMENTS

TW    200638929 A    11/2006

OTHER PUBLICATIONS

Chih-Hsin Lin, Yih-Ru Wu, Pin-Jui Kung, Wan-Ling Chen, Li-Ching Lee, Te-Hsien Lin, Chig-Ying Chao, Chiung-Mei Chen, Kuo-Hsuan Chang, Donala Janreddy, Guey-Jen Lee-Chen and Ching-Fa Yao, The Potential of Indole and a Synthetic Derivative for PolyQ Aggregation Reduction by Enhancement of the Caperone and Autophagy Systems, ACS Chem. Neurosci. 2014, 5, 1063-1074.

Kung Pin-Jui, Tao Yu-Chen, Hsu Ho-Chiang, Chen Wan-Ling, Lin Te-Hsien, Janreddy Donala, Yao Ching-Fa, Chang Kuo-Hsuan, Lin Jung-Yaw, Su Ming-Tsan, Wu Chung-Hsin, Lee-Chen Guey-Jen, Hsieh-Li Hsiu-Mei, Indole and synthetic derivative activate chaperone expression to reduce polyQ aggregation in SCA17 neuronal cell and slice culture models, Drug Design, Development and Therapy 2014:8 1929-1939.

Janreddy et al., "An Easy Access to Carbazolones and 2,3-Disubstituted Indoles", Eur. J. Org. Chem., 2011, pp. 2360-2365.

Wu et al., "Analysis of heat-shock protein 70 gene polymorphisms and the risk of Parkinson's disease", Hum Genet, 2004, 114, pp. 236-241.

Zhang et al., "Structural Organization and Promoter Analysis of Murine Heat Shock Transcription Factor-1 Gene", The Journal of Biological Chemistry, 1998, vol. 273, No. 49, Issue of Dec. 4, pp. 32514-32521.

Sole et al., "3a-(o-Nitrophenyl)octahydroindol-4-ones: Synthesis and Spectroscopic Analysis", Tetrahedron, 1996, vol. 52, No. 11, pp. 4013-4028.

He et al., "Genetic Variations in HSPA8 Gene Associated with Coronary Heart Disease Risk in a Chinese Population", PLoS One, Mar. 2010, vol. 5, Issue 3, e9684, pp. 1-7.

*Primary Examiner* — Yong Chong
(74) *Attorney, Agent, or Firm* — Bacon & Thomas, PLLC

(57) ABSTRACT

A method for treating an abnormal polyglutamine-mediated disease is disclosed, wherein indole and an indole-based compound contained in a pharmaceutical composition used in the method of the present invention can reduce the polyglutamine aggregation through decreasing reactive oxygen species production and increasing the activity of chaperone and autophagy.

9 Claims, 17 Drawing Sheets

Indole

Chemical Formula: $C_8H_7N$
Molecular weight: 117.15

NC001-2

Chemical Formula: $C_{13}H_{13}NO_2$
Molecular Weight: 215.2478

NC001-3

Chemical Formula: $C_{14}H_{15}NO$
Molecular Weight: 213.2750

NC001-8

Chemical Formula: $C_{11}H_9NO$
Molecular Weight: 171.1953

NC001-11

Chemical Formula: $C_{22}H_{17}NO_2$
Molecular Weight: 327.3759

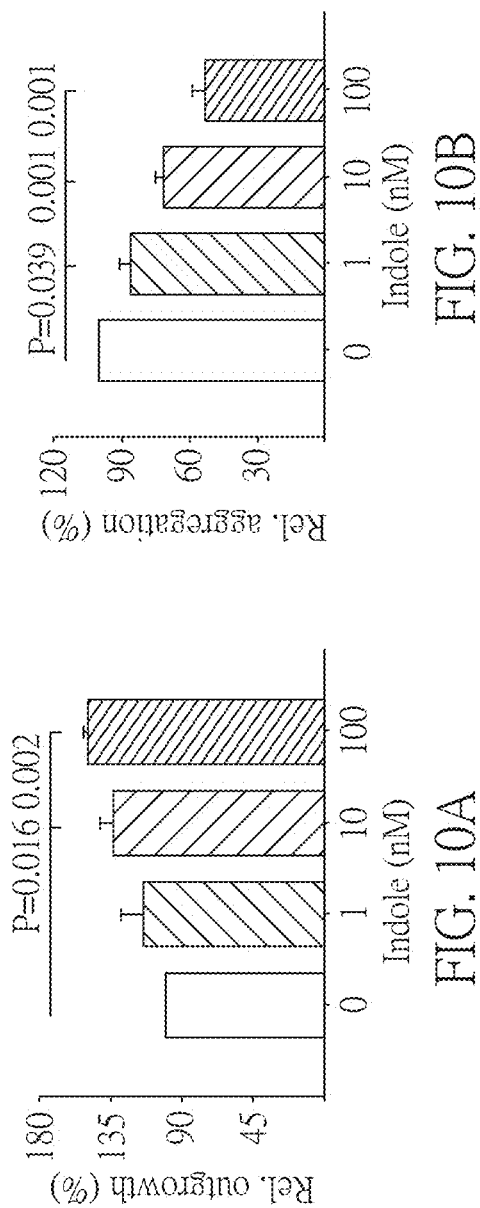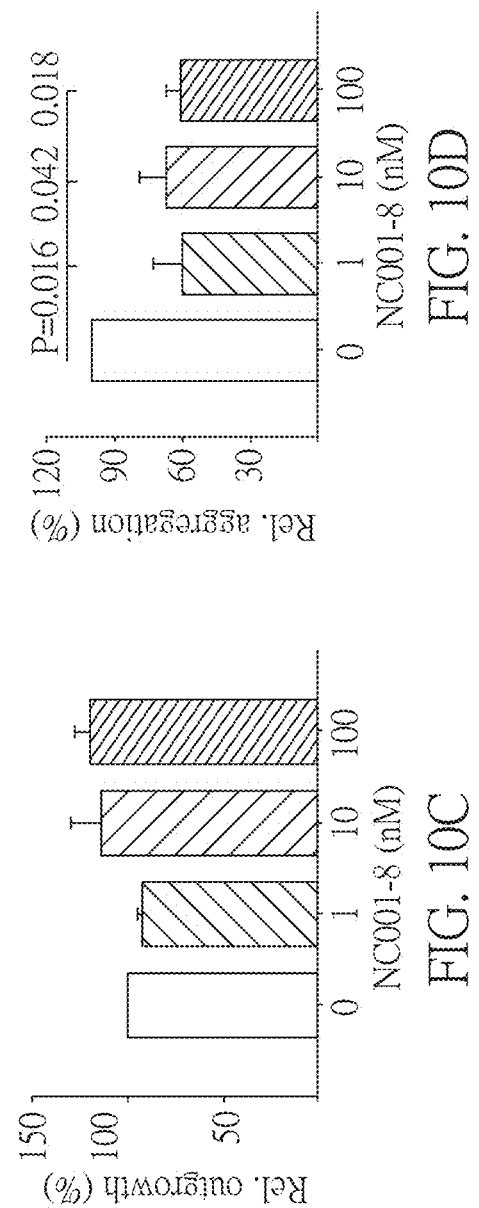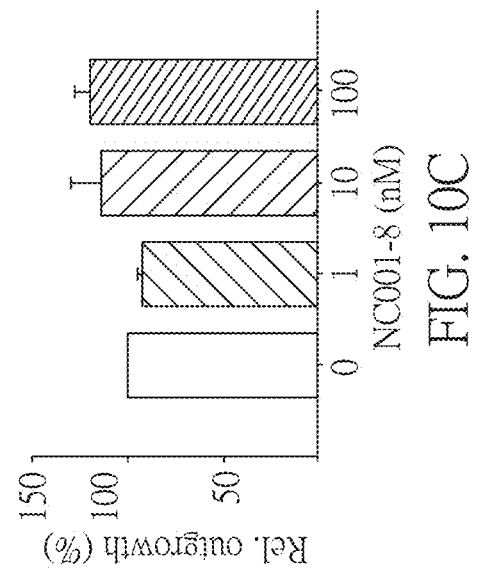

METHOD FOR TREATING ABNORMAL POLYGLUTAMINE-MEDIATED DISEASE

CROSS REFERENCE TO RELATED APPLICATION

This application claims the benefits of the Taiwan Patent Application Serial Number 102119511, filed on May 31, 2013, the subject matter of which is incorporated herein by reference.

BACKGROUND OF THE INVENTION

1. Field of the Invention

The present invention related to a method for treating abnormal polyglutamine (polyQ)-mediated disease with a pharmaceutical composition comprising specific indole-based compound, which can reduce the amount of reactive oxygen species, enhance chaperone activity, and enhance autophagy activity to achieve the purpose of suppressing aggregation of polyglutamine in a subject in need.

2. Description of Related Art

The spinocerebellar atrophy is referred as spinocerebellar ataxias (SCAs), which is a complex group of heterogeneous autosomal dominant neurodegenerative disorder. Spinocerebellar ataxias (SCAs) are caused by expanded CAG repeats encoding a long polyQ tract in mutant proteins, and the misfolded polyQ proteins accumulate in the nucleus and cytoplasm of neural cells. The clinical symptom of spinocerebellar atrophy comprises cerebellar degeneration, dysfunctions of nervous system and other parts.

On the current market, there is no drug for curing or suppressing polyglutamine related spinocerebellar ataxia progression, and the symptom thereof is irreversible: patients may fail to appropriately control their movements at the beginning; with the deterioration of disease condition, patients become failing to walk and write progressively, and finally become failing to talk and swallow. In the worst case, it may bring patients to an end with death. However, even though there is atrophy of the cerebellum, the brainstem, and the spinal cord, the intelligence is completely unaffected, so that patients can be clearly conscious of the fact that their bodies gradually become inactive.

In view of the gradually increased global population suffering from cerebellar atrophy, what is needed is to find a compound capable of reducing the accumulation of polyglutamine to be used for the manufacture of pharmaceutical compositions for abnormal accumulated polyglutamine-mediated diseases, to serve as an adjuvant therapy for neurodegenerative disease, such as cerebellar atrophy, thereby effectively slowing down the disease progression, as well as providing the patients with a better quality of life.

SUMMARY OF THE INVENTION

An object of the present invention is to provide a method for treating an abnormal polyglutamine-mediated disease to give assistance to the treatment of neurodegenerative disease like spinocerebellar ataxia.

Another object of the present invention is to provide a method for reducing reactive oxygen species, enhancing chaperone activity, and enhancing autophagy activity to achieve the purpose of suppressing aggregation of polyglutamine in a subject in need.

To achieve the object, the present invention provides a pharmaceutical composition for treating an abnormal polyglutamine-mediated disease, which comprises: at least one compound selected from the group consisting of the following formula 1, a compound of the following formula 2, and derivatives thereof.

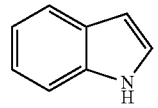

[Formula 1]

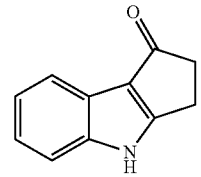

[Formula 2]

In the abnormal polyglutamine-mediated disease, the expanded polyglutamine tracts in respective proteins increase reactive oxygen species and further lead to protein misfolding and subsequent aggregation, resulting in the clearance of the misfolding and aggregated proteins via suppressing chaperone and the autophagy pathways. Hence, the aforementioned compound represented by the formula 1 or 2 can reduce reactive oxygen species, enhance chaperone activity, and enhance the autophagy activity to solve the aforementioned problems.

In the present invention, the type of the abnormal polyglutamine-mediated disease is not particularly limited. Preferably, the abnormal polyglutamine-mediated disease is spinocerebellar ataxia. In spinocerebellar ataxia, the expansions of CAG trinucleotide repeats encoding a polyglutamine stretch have been shown to cause dominantly inherited SCA1, SCA2, SCA3, SCA6, SCAT, SCA8, SCA17 and dentatorubropallidoluysian atrophy (DRPLA). These polyQ-mediated genetic disorders in SCAs have shown selective progressive degeneration of the cerebellum, brainstem, and spinal cord tract, with prominent pathological hallmark of intranuclear and cytoplasmic accumulation of aggregated polyQ proteins inside degenerated neurons, thereby causing the dysfunction and degeneration of specific neurons.

In addition, the used concentration of the aforementioned compound represented by the formula 1 or 2 is not particularly limited, and can be adjusted according to actual situation for use, such as the severity of the diseases or used complementary drugs. In a preferred embodiment of the present invention, the concentration of the formula 1 or 2 is preferably in a range from 1 nM to 50 µM, and more preferably in a range from 10 nM to 10 µM in the pharmaceutical composition.

In the present invention, the aforementioned compound represented by the formula 1 or 2 can enhance chaperone activity to decrease polyglutamine misfolding and subsequent aggregation in the subject in need, which may be accomplished by activating heat shock transcription factor 1 (HSF 1), heat shock cognate protein (HSPA8), or heat-inducible HSP70 chaperone (HSPA1A).

In the present invention, the aforementioned compound represented by the formula 1 or 2 can enhance the autophagy activity, which may be accomplished by increasing the expression of autophagosomes and a ratio of LC3-II (light-chain 3 protein-II) to LC3-I (light-chain 3 protein-I) (LC3-II/LC3-I).

Hence, the present invention further provides a method for treating an abnormal polyglutamine-mediated disease, which comprises: administering a pharmaceutical composition comprising at least one compound represented by the formula 1 or 2 to a subject in need.

It should be noted that the derivatives of the aforementioned compound represented by the formula 1 or 2 may also have the same efficacy. The examples of the derivatives thereof can be obtained through any chemical modification generally used in the art.

The aforementioned compound represented by the formula 1 or 2 can be obtained commercially or prepared through chemical synthesis generally used in the art. For example, the compound can be prepared by the method described in references (Sole D, Bosch J, Bonjoch J, Tetrahedron, vol. 52, No. 11, pp. 4013-4028, 1996; and Janreddy D, Kavala V, Bosco J W J, Kuo C W, Yao C F, European Journal of Organic Chemistry, pp. 2360-2365, 2011) with suitable modifications, which a person skilled in the art can refer to.

The term "inhibit", "reduce" or "decrease" used herein refers to the case that the pharmaceutical composition including the indole-based compound represented by the formula 1 or 2 of the present invention is applied to a subject suffering from abnormal polyglutamine-mediated disease (such as spinocerebellar ataxia), having symptom of abnormal polyglutamine-mediated disease, or having a tendency of development of abnormal polyglutamine-mediated disease, in order to achieve the treatment, mitigation, slowing, therapy, improvement, or recovery of the tendency of the disease and symptoms.

To implement the method according to the present invention, the above pharmaceutical composition can be administered via oral administering, parenteral administering, inhalation spray administering, topical administering, rectal administering, nasal administering, sublingual administering, vaginal administering, or implanted reservoir, and so on. The term "parenteral" used here refers to subcutaneous injection, intradermal injection, intravenous injection, intramuscular injection, intraarticular injection, intraarterial injection, joint fluid injection, intrathoracic injection, intrathecal injection, injection at morbid site, and intracranial injection or injection technique.

In addition, the pharmaceutical composition containing the aforementioned compound can be formulated into health foods or clinical drugs for preventing and treating abnormal polyglutamine-mediated diseases through any medicine manufacturing procedure. According to the requirement for use, the pharmaceutical composition of the present invention may further comprise at least one of a pharmaceutically acceptable carrier, a diluent, or an excipient in the art. For example, the aforementioned compound is encapsulated into liposome to facilitate delivery and absorption; the aforementioned compound is diluted with aqueous suspension, dispersion or solution to facilitate injection; or the aforementioned compound is prepared in a form of a capsule or tablet for storage and carrying.

More specifically, the pharmaceutical composition of the present invention can be formulated into a solid form or a liquid form. The solid dosage formulations may comprise: powders, pellets, tablets, capsules, and suppositories, but the present invention is not limited thereto. In addition, excipients, flavoring agents, preservatives, disintegrants, flow aids, and fillers may be comprised in the solid dosage formulation, but the present invention is not limited thereto. The liquid dosage formulations may comprise: water, solution (such as propylene glycol solution), suspension, and emulsifier; and suitable coloring agents, flavoring agents, stabilizers and thickening agents may also be used to prepare the liquid dosage formulations.

For example, the powder formulation can be prepared by mixing the compound of the present invention with a suitable pharmaceutical acceptable excipient (such as sucrose, starch and microcrystalline cellulose). The pellet formulation can be prepared by mixing the compound of the present invention with a suitable pharmaceutical acceptable excipient and a suitable pharmaceutical acceptable binder (such as polyvinyl pyrrolidone and hydroxypropyl cellulose), followed by wet granulation with a solvent (such as water, alcohol and isopropanol) or dry granulation with pressure. In addition, the tablet formulation can be prepared by mixing the pellet formulation with a suitable pharmaceutical acceptable flow aids (such as magnesium stearate), followed by pressing with a tablet press machine. Therefore, the administered formulations can be selected according to the subject's requirement.

Other objects, advantages, and novel features of the invention will become more apparent from the following detailed description when taken in conjunction with the accompanying drawings.

BRIEF DESCRIPTION OF THE DRAWINGS

FIGS. 10A and 10B respectively show the neuronal outgrowth and aggregation analysis from microscopic images of primary cultured Purkinje cell from SCA17 mouse cerebellum after indole treatment according to one preferred embodiment of the present invention;

FIGS. 10C and 10D respectively show the neuronal outgrowth and aggregation analysis from microscopic images of primary cultured Purkinje cell from SCA17 mouse cerebellum after NC001-8 treatment according to one preferred embodiment of the present invention.

DETAILED DESCRIPTION OF THE PREFERRED EMBODIMENT

[Indole and Derivatives Thereof]

Figure 1:
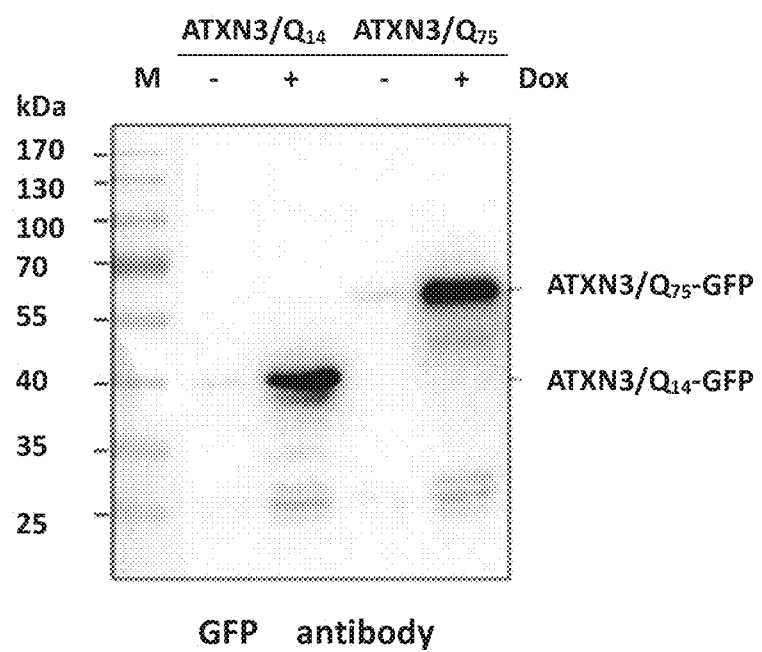
FIG. 1 shows a result of Western blot analysis of ATXN3/$Q_{14\sim75}$-GFP protein expression induced with doxycycline according to one preferred embodiment of the present invention.

We used indole (commercial available) and synthesized derivatives (NC001-2, NC001-3, NC001-8 and NC001-11) thereof. First, 1.0 eq. 1,3-cyclopentanedione, 1.5 eq. anhydrous potassium carbonate, and 0.5 eq. o-iodonitrobenzene were placed in proper amounts of dimethyl sulfoxide, and heated under 85-90° C. for 4 hours. After the reaction was completed, the solution was cooled down to the room temperature and then poured into ice-cold saline solution. The solution was extracted with dichloromethane several times; and liquid extract of dichloromethane was washed using ice-cold saline solution, dried out using anhydrous magnesium sulphate, filtered, and concentrated. The liquid concentrate of mixture was purified and separated by flash column chromatography, and the intermediate, 2-(o-nitrobenzene)-1,3-cyclopentanedione or 3-hydroxy-2-(2-nitrophenyl)cyclopentenone, which are co-existed structural isomers, was obtained.

Next, 1.0 eq. 2-(o-nitrobenzene)-1,3-cyclopentanedione was added into proper amounts of acetic acid solution, and heated until the solution turned into homogeneous phase. Six eq. iron powder was further added into the solution and the reaction was performed under reflux. The reactive level was traced using thin layer chromatography during the reaction. After the reaction was completed, the solution was cooled down to the room temperature and then poured into ice-cold saline solution. The solution was extracted with ethyl acetate several times; and liquid extract of dichloromethane was filtered by celite to remove the excess iron powder, dried out using anhydrous magnesium sulphate, filtered, and concentrated. The liquid concentrate of mixture was purified and separated by flash column chromatography, and 3,4-dihydrocyclopenta[b]indol-1(2H)-one was obtained, which was referred as "NC001-8" hereinafter. Besides, other derivatives named "NC001-2, NC001-3, and NC001-11" were synthesized with the similar protocol.

[Cell Cultured and Cytotoxicity Analysis]

Human embryonic kidney HEK-293 cells (ATCC No. CRL-1573) were cultivated in Dulbecco's modified Eagle's medium (DMEM) containing 10% fetal bovine serum (FBS). Human neuroblastoma SH-SY5Y cells (ATCC No. CRL-2266) were maintained in DMEM F12 supplemented with 10% FBS. Cells were cultivated at 37° C. incubator containing 5% $CO_2$ and cell proliferation was measured based upon the reduction of the tetrazolium salt, 3,[4,5-dimethylthiazol-2-yl]-2,5-diphenyl-tetrazolium bromide (MTT). Cells were plated into 48-well ($5\times10^4$/well) dishes, grown for 20 hours and treated with different concentrations of indole and derivatives thereof, geranylgeranylacetone (GGA, Sigma), or suberoylanilide hydroxamic acid (SAHA, Cayman Chemical) (0.1 μM~1 mM). After one day, 20 μL MTT (5 mg/mL in PBS, Sigma) was added to cells and incubated for 2 hours. The absorbance of the purple formazan dye was measured at 570 nm by a Bio-Tek μtQuant Universal Microplate Spectrophotometer.

[ATXN3 cDNA Constructs]

Polyadenylated RNA (200 ng) isolated from neuroblastoma SK-N-SH cells was reverse transcribed using the SuperScript™ III reverse transcriptase (Invitrogen). The sense and antisense primers used for ATXN3/$Q_{14}$ cDNA (+826~+1152, NM_004993) amplification were 5'-ATTCAGCTAAGT <u>ATG</u>CAAGGTAGTTCCA (codon for Met257 underlined, SEQ ID NO: 1) and 5'-CATG<u>CCATGG</u>CATGTTTTTTC CTTCTGTT (NcoI site underlined, SEQ ID NO: 2).

The amplified 3' polyQ-containing cDNA fragment (translated into amino acids 257~361) was cloned into pGEM-T Easy (Promega) and sequenced. The ATXN3/$Q_{14}$ cDNA was excised with EcoRI (in pGEM-T Easy vector) and NcoI and subcloned into pEGFP-N1 (Clontech). Then, DNA fragment containing in-frame ATXN3/$Q_{14}$-EGFP was excised with HindIII-NotI and subcloned into the pcDNA5/FRT/TO. The ATXN3/$Q_{75}$ cDNA was made by replacing an 88 bp ATXN3/$Q_{14}$ BsmBI-BsmFI fragment with a 271 bp ATXN3/$Q_{75}$ fragment from the cDNA clone of a SCA3 patient.

[Isogenic 293 and SH-SY5Y Cell Lines]

The cloned pcDNA5/FRT/TO-nTBP/$Q_{36\sim79}$-GFP plasmids were used to generate the isogenic TBP cell lines by targeting insertion into Flp-In SH-SY5Y cells. The cloned plasmids and pOG44 (Invitrogen) plasmid for expression Flp recombinase were co-transfected into the aforementioned SH-SY5Y host cell lines by using the liposome-mediated transfection (LF2000, Invitrogen). In addition, the cloned pcDNA5/FRT/TO-ATXN3/$Q_{14}$ and $Q_{75}$ plasmids were used to generate the isogenic ATXN3/$Q_{14\sim75}$ cell lines by targeting insertion into Flp-In™ 293 cells. The aforementioned cell lines were grown in medium containing 5 μg/mL blasticidin and 100 μg/mL hygromycin (InvivoGen).

[ATXN3/$Q_{75}$ Aggregation Assay]

293 ATXN3/$Q_{75}$-GFP cells were plated into 96-well ($2\times10^4$/well) dishes, grown for 24 hr and treated with different concentrations of the indole or derivatives thereof dissolved in 0.1% DMSO (100 nM-1 μM), GGA, and SAHA for 8 hr. Then, doxycycline (10 μg/mL, BD) was added to the medium in each well to induce ATXN3/$Q_{75}$-GFP expression for 6 days. Oxaliplatin (5 μM, Sigma) was also added to increase aggregate accumulation through inhibition of cell division. Then, cells were stained with Hoechst 33342 (0.1 μg/mL, Sigma) and aggregation percentage was assessed by high content analysis (HCA) system (ImageXpressMICRO, Molecular Devices), with excitation/emission wavelengths at 482/536 (EGFP).

[Generation of Flp-In™-293 Triple Fluorescent Reporter Cells]

Referring to three references (Zhang Y, Koushik S, Dai R, Mivechi N F, Journal of Biological Chemistry, vol. 273, no. 49, pp. 32514-32521, 1998; He M, Guo H, Yang X, Zhou L, Zhang X, Cheng L, Zeng H, Hu F B, Tanguay R M, Wu T, PLoS One, vol. 5, no. 3, e9684, 2010; and Wu Y R, Wang C K, Chen C M, Hsu Y, Lin S J, Lin Y Y, Fung H C, Chang K H, Lee-Chen G J, Human Genetics, vol. 114, no. 3, pp. 236-241, 2004), a triple fluorescent reporter plasmid was constructed in pAmCyan1-N1 with mCherry, ZsYellow1 and AmCyan1 fluorescent reporters driven by heat shock transcription factor1 (HSF1, −360~+2, with the translation initiation A as +1), heat shock cognate protein (HSPA8, −1140~+38, driving constitutively expressed HSP70) and heat-inducible HSP70 chaperone (HSPA1A, −273~+215, driving heat-inducible HSP70) promoters, respectively. The fragment containing the HSF1, HSPA8 and HSPA1A driven reporters was removed with AseI and NotI restriction enzymes and used to replace an AseI-NotI fragment in pcDNA5/FRT/TO plasmid (Invitrogen). The resulting triple fluorescent reporter plasmid was used to generate triple fluorescent reporter cells by targeted insertion into Flp-In™-293 cells, according to the supplier's instructions (Invitrogen). The cells were selected by medium containing 5 µg/mL blasticidin S and 100 µg/mL hygromycin.

The triple fluorescent reporter cells ($5 \times 10^4$/well in 96-well plate) were incubated for 2 days and then treated with GGA (control), indole, or NC001-8 derivative thereof (100 nM-100 µM) for 24 hours. The three fluorescence colors were analyzed simultaneously using high-content analysis (HCA) system (ImageXpressMICRO, Molecular Devices), with excitation/emission wavelengths at 453/486 (mCherry), 531/540 (ZsYellow1) and 587/610 nm (AmCyan1).

[Western Blot Analysis]

Total proteins were prepared using lysis buffer containing 50 mM Tris-HCl, 150 mM NaCl, 1 mM EDTA, 1 mM EGTA, 0.1% SDS and 0.5% sodium deoxycholate, 1% Triton X-100, and protease inhibitor cocktail (Calbiochem). Proteins (25 µg) were separated on 10% SDS-polyacrylamide gel electrophoresis and blotted on to nitrocellulose membranes by reverse electrophoresis. After blocking, the membrane was probed with antibody to HSF1 (1:1000 dilution, Abnova), HSPA8 (1:500 dilution, Santa Cruz), HSPA1A (1:500 dilution, Santa Cruz), GFP (1:500 dilution, Santa Cruz), LC3 (1:3000 dilution, MBL International), TBP (N-12) (1:500 dilution, Santa Cruz), β-actin (1:5000 dilution, Millipore) or GAPDH (1:1000 dilution, MDBio) at 4° C. overnight. Then the immune complexes were detected by horseradish peroxidase-conjugated goat anti-mouse (Jackson ImmunoResearch) or goat anti-rabbit (Rochland) IgG antibody (1:5000 dilution, GeneTex) and chemiluminescent substrate (Millipore).

293 ATXN3/$Q_{75}$-GFP cells were incubated for 24 hours ($10^5$/well in 6-well plate), and then treated with 100 nM indole and derivatives thereof for 8 hours before induced with 10 µg/mL doxycycline to express ATXN3/$Q_{75}$-GFP. Oxaliplatin (5 µM, Sigma) was also added to increase aggregate accumulation through inhibition of cell division. After 6 days, 5 µM fluorescent reagent (CellROX™ Deep Red Reagent, Molecular Probes) was added and maintained at 37° C. for 30 minutes. Cells were washed using PBS, and green fluorescence of $5 \times 10^4$ cells was analyzed under excitation/emission at 488/507 nm (that is, the ATXN3/$Q_{75}$-GFP expression) and red fluorescence of $5 \times 10^4$ cells was analyzed under excitation/emission at 640/665 nm (that is, the amount of reactive oxygen species) using FACSCalibur flow cytometer (Becton-Dickinson).

[Real-Time PCR]

Total RNA from SH-SY5Y TBP/$Q_{36-79}$ cells was extracted using Trizol reagent (Invitrogen). The RNA was DNase (Stratagene) treated, quantified, and reverse-transcribed to cDNA. Real-time quantitative PCR experiments were performed in the ABI PRISM® 7000 Sequence Detection System (Applied Biosystems). Amplification was performed on 12.5 ng cDNA with gene-specific TaqMan fluorogenic probes Hs00920494_ml for TBP and 4326321E for HPRT1 (endogenous control) (Applied Biosystems). Fold change was calculated using the formula $2^{\Delta Ct}$, $\Delta C_T = C_T$ (control)$-C_T$ (target), in which $C_T$ indicates cycle threshold.

[SCA17 Mouse Cerebellar Primary Cultures]

The medium was prepared based on NEUROBASAL®medium (Invitrogen) and further contained 2% B-27 (v/v, Invitrogen), 1 mM adenine (Sigma), 2 mM GlutaMax-I (Invitrogen), 3 mM KCl (Sigma), 5 µg/mL gentamicin (Invitrogen), 100 U/mL penicillin, and 100 µg/mL streptomycin (Invitrogen). Cerebellum was separated from newborn SCA17 mice (born within 1 day), shredded and placed into medium containing 0.05% trypsin/EDTA (Invitrogen) and 20 U/mL DNase (Sigma). After 15 minutes at 37° C., centrifuged and the supernatant was removed. Medium containing 10% fatal bovine serum (FBS, Invitrogen) and 20 U/mL DNase I (Sigma) were added to stop protein degradation, and then cells were washed using medium without serum. The cells were suspended in medium containing 10% FBS and seeded in 96-well plate coated with poly-L-lysine (Sigma). The medium was replaced with medium without serum at day 2. After culture for 5 days, cells were treated with 4 µM cytosine arabinoside (AraC) and various concentrations of drugs; and cells were fixed using 4% paraformaldehyde at day 8. Cells were immunostained with primary antibody [IP3R-1 (for Purkinje cells), 1:1000, Santa Cruz; 1TBP18 (for aggregation), 1:30000, QED Bioscience], fluorescence-conjugated secondary antibody (1:500, Invitrogen) and DAPI (1:10000, Sigma). The staining was assessed by automated inverted research microscope (Leica DMI 4000) and high content analysis (HCA) system (ImageXpressMICRO, Molecular Devices).

[SCA17 Mouse Cerebellar Slice Cultures]

Cerebellum was separated from p7 SCA17 mice and transferred to ice-cold medium containing 50% basal medium eagle (Invitrogen), 25% Hank's buffered salt solution (Invitrogen), 25% horse serum (Invitrogen), 0.5% D-glucose (Sigma), 1 mM GlutaMAX I (Invitrogen), 100 U/mL penicillin (Invitrogen) and 100 µg/mL streptomycin (Invitrogen). The cerebellum was separated from the other brain regions in ice-cold medium, and the hemisphere was then cut into 350 µm parasagittal sections with a vibratome (VT1200S, Leica). To improve the survival rate of cerebellar slices, we continuously bubbled the medium with 95% $O_2$ and 5% $CO_2$ during the sectioning. The slices were then cultured on 0.4 µm pore size culture plate inserts (Millipore) in six-well plates. All treatments were applied to the slices at day 2. After culture for 7 days, cells were immunostained with primary antibody [IP3R-1 (for Purkinje cells), 1:1000, Santa Cruz; 1TBP18 (for aggregation), 1:30000, QED Bioscience], fluorescence-conjugated secondary antibody (1:500, Invitrogen) and DAPI (1:10000, Sigma). The staining results were observed by confocal microscope (DMRE, TCS SP2, Leica).

[Statistical Analysis]

For each set of values, data were expressed as the means±standard deviation (SD). Three independent experiments were performed and non-categorical variables were compared using the Student's t-test. All P-values were two-tailed, with values of P<0.05 considered significant.

[Results]

[Construction of 293 Cells Expressing ATXN3/$Q_{75}$ Aggregates]

In the present example, GFP-tagged ATXN3 C-terminal $Q_{14\sim75}$-containing fragment was cloned to establish Flp-In 293 cells with ATXN3/$Q_{14\sim75}$-GFP expression in an inducible fashion, wherein ATXN3/$Q_{14}$ was used as a control. As shown in FIG. 1, the GFP antibody detected 40 kDa ATXN3/$Q_{14}$-GFP and 57 kDa ATXN3/$Q_{75}$-GFP proteins in doxycycline (Dox) induced ATXN3 cells.

[Cytotoxicity of Indole-based Compounds]

Figure 2A:
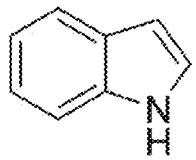
FIG. 2A shows structures, formulas, and molecular weights of the indole-based compounds used in one preferred embodiment of the present invention.
Figure 2A:
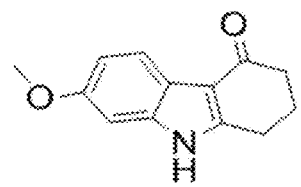
Figure 2A:
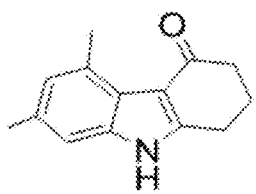
Figure 2A:
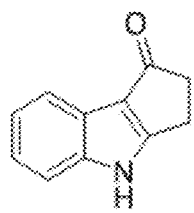
Figure 2A:
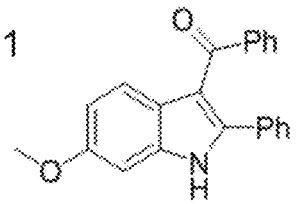
Figure 2B:
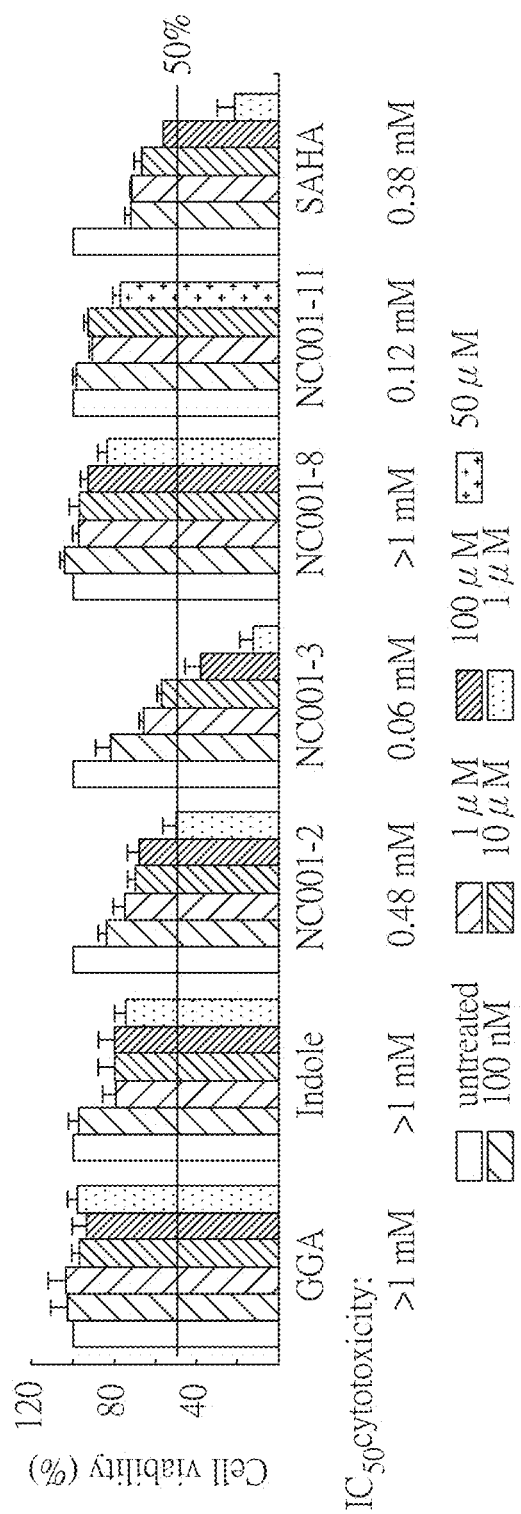
FIG. 2B shows a result of cytotoxicity of the indole-based compounds against HEK-293 cells in one preferred embodiment of the present invention.
Figure 2C:
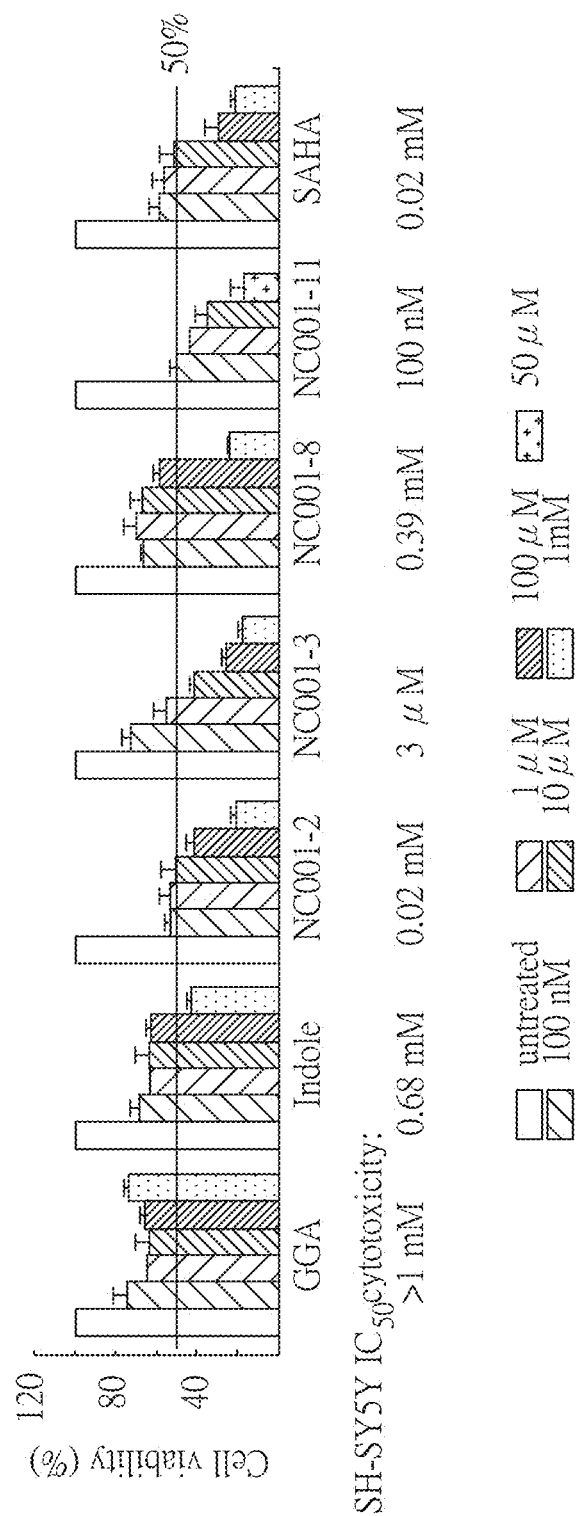
FIG. 2C shows a result of cytotoxicity of the indole-based compounds against SH-SY5Y cells in one preferred embodiment of the present invention.

The structures, formulas and molecular weights of indole and derivatives NC001-2, NC001-3, NC001-8, and NC001-11 are shown in FIG. 2A. In MTT assays, the results of cytotoxicity, in which the treatment with indole and derivatives thereof, GGA, and SAHA against human embryonic kidney 293 and human neuroblastoma SH-SY5Y cells treated with for 24 hours, were shown in FIGS. 2B and 2C. The histone deacetylase inhibitor SAHA known to reduce SDS-insoluble polyQ aggregates was included for comparison. GGA was a positive control to enhance chaperone activity and induce HSPs expression. The $IC_{50}$ of the indole and derivatives thereof, GGA, and SAHA were calculated using the interpolation method.

Among the tested compounds, GGA, indole, and NC001-8 had an $IC_{50}$ higher than the highest concentration tested (>1 mM) against HEK-293 cells; and the $IC_{50}$ of GGA, indole, and NC001-8 respectively were 1 mM, 0.68 mM, and 0.39 mM against SH-SY5Y cells; suggesting their very low cytotoxicity.

[Effect of Indole and Derivatives on ATXN3/$Q_{75}$ Aggregation in Flp-In 293 Cell Model]

Figure 3:
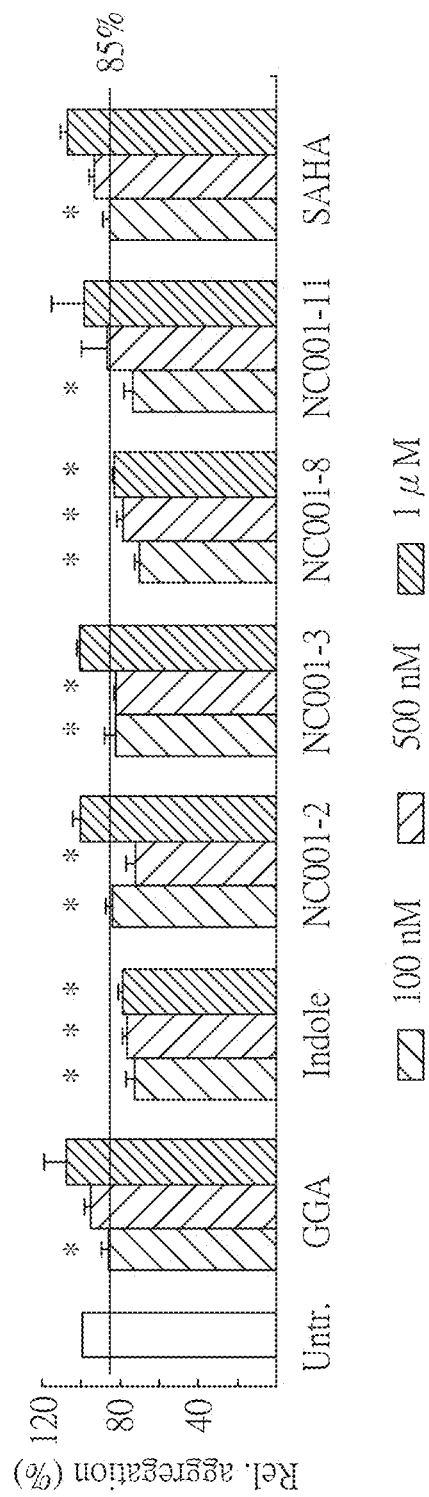
FIG. 3 shows a result of polyQ aggregation analysis of ATXN3/$Q_{14\sim75}$-GFP cells treated with the indole-based compounds according to one preferred embodiment of the present invention.

In the present example, the influences of indole and derivatives thereof, GGA, and SAHA in the ATXN3/$Q_{75}$-GFP cells were respectively examined. After 6 days of the treatment of doxycycline and oxaliplatin, the fluorescence microscopy images were observed, and aggregation percentage of ATXN3/$Q_{75}$-GFP cells was assessed by high-content analysis system. The result was shown in FIG. 3, as a positive control, GGA and SAHA reduced the ATXN3/$Q_{75}$ aggregation to 85% (at 100 nM) as compared to untreated cells (100%). Both indole and derivatives displayed good aggregation-inhibitory potential at 100 nM~1 μM (73~79% for indole and 70~84% for NC001-8), 100~500 nM (84~73% for NC001-2 and 83% for NC001-3), or 100 nM (74% for NC001-11). The $IC_{50}$ cytotoxicity vs. most effective (reduced the ATXN3/$Q_{75}$ aggregation to 85% or lower) dose ratio of GGA, indole, NC001-2, NC001-3, NC001-8, NC001-11 and SAHA are >10000, >10000, 960, 600, >10000, 1200 and 3800, respectively.

[Effect of Indole and Derivatives Enhanced HSF1 and HSP70 Chaperone Expression in Flp-In 293 Cell Model]

Figure 4A:
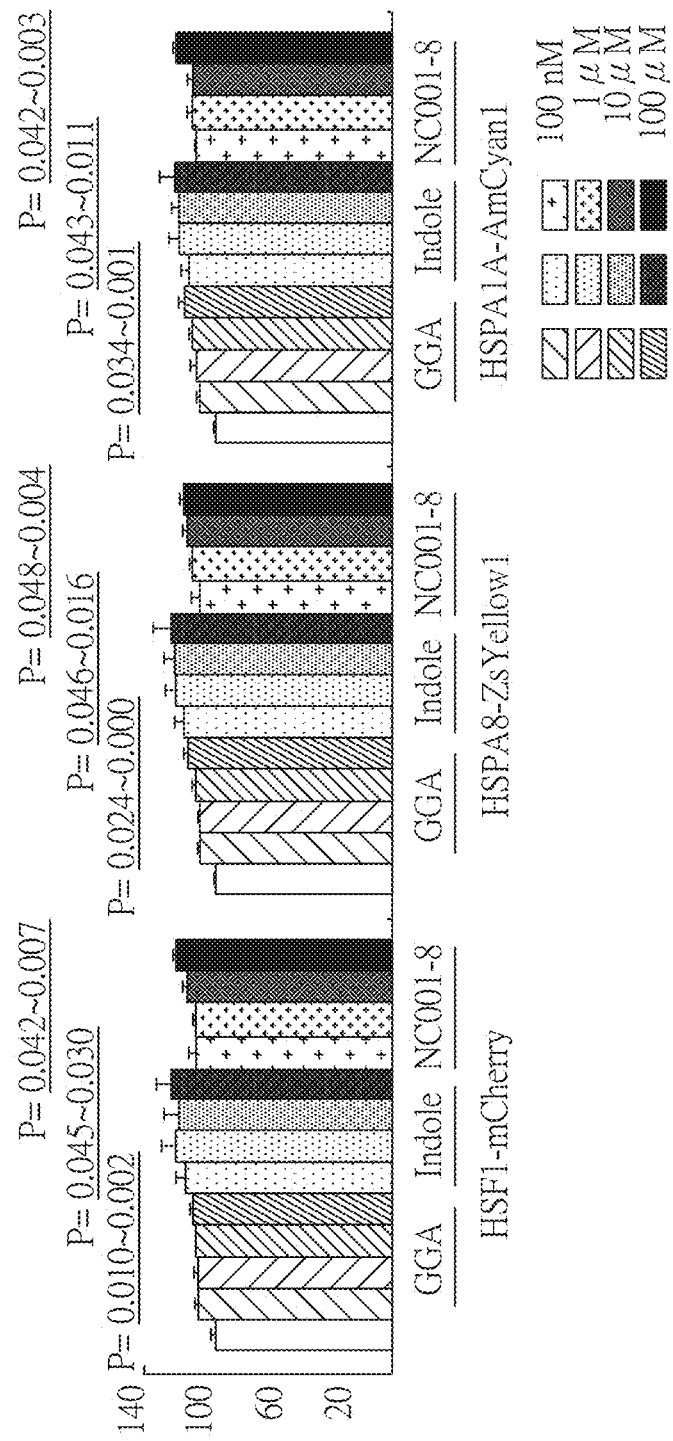
FIG. 4A shows fluorescence level of triple fluorescent reporter cell after treatment with the indole-based compounds according to one preferred embodiment of the present invention.
Figure 4B:
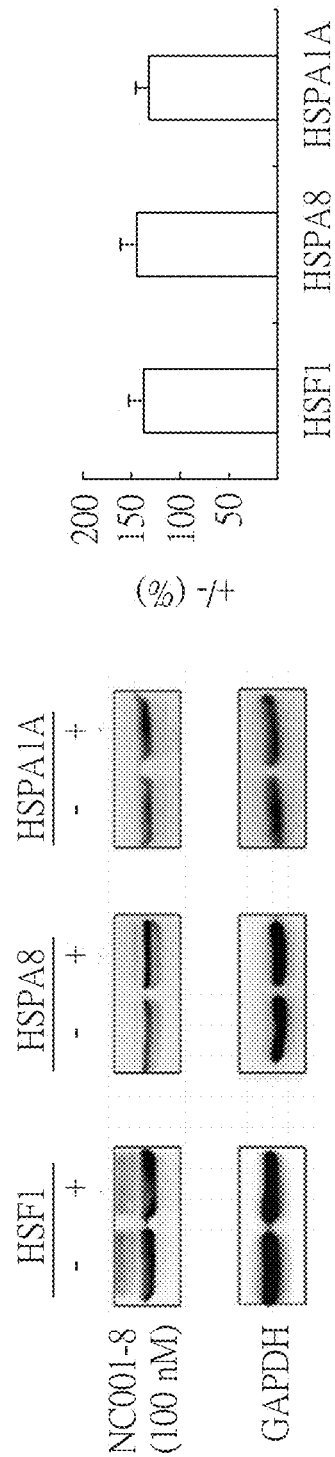
FIG. 4B shows a result of Western blot analysis of HEK-293 cells after treatment with the indole-based compounds according to one preferred embodiment of the present invention.

The triple fluorescent reporter cells were used to screen the potential of indole and derivatives for enhancing HSF 1 and HSP70 chaperone expression. As shown in FIG. 4A, treatment of GGA showed enhanced HSF1 (P=0.010~0.002), HSPA8 (P=0.024~0.000) and HSPA1A (P=0.034~0.001) promoter activities. Treatment of indole and NC001-8 showed the same trend of enhancement on HSF1, HSPA8 and HSPA1A promoter activities (indole: HSF1 (P=0.045~0.030), HSPA8 (P=0.046~0.016), and HSPA1A (P=0.043~0.011); NC001-8: HSF1 (P=0.042~0.007), HSPA8 (P=0.048~0.004), and HSPA1A (P=0.042~0.003)). Besides, the enhancement of NC001-8 on HSF1, HSPA8, and HSPA1A expression (132%~144%, P=0.046~0.042) was further confirmed by the Western blot in HEK-293 cells after two days treatment (FIG. 4B).

[Indole and Derivatives Enhanced Chaperone Expression on 293 ATXN3/$Q_{75}$ Cell Model]

Figure 5:
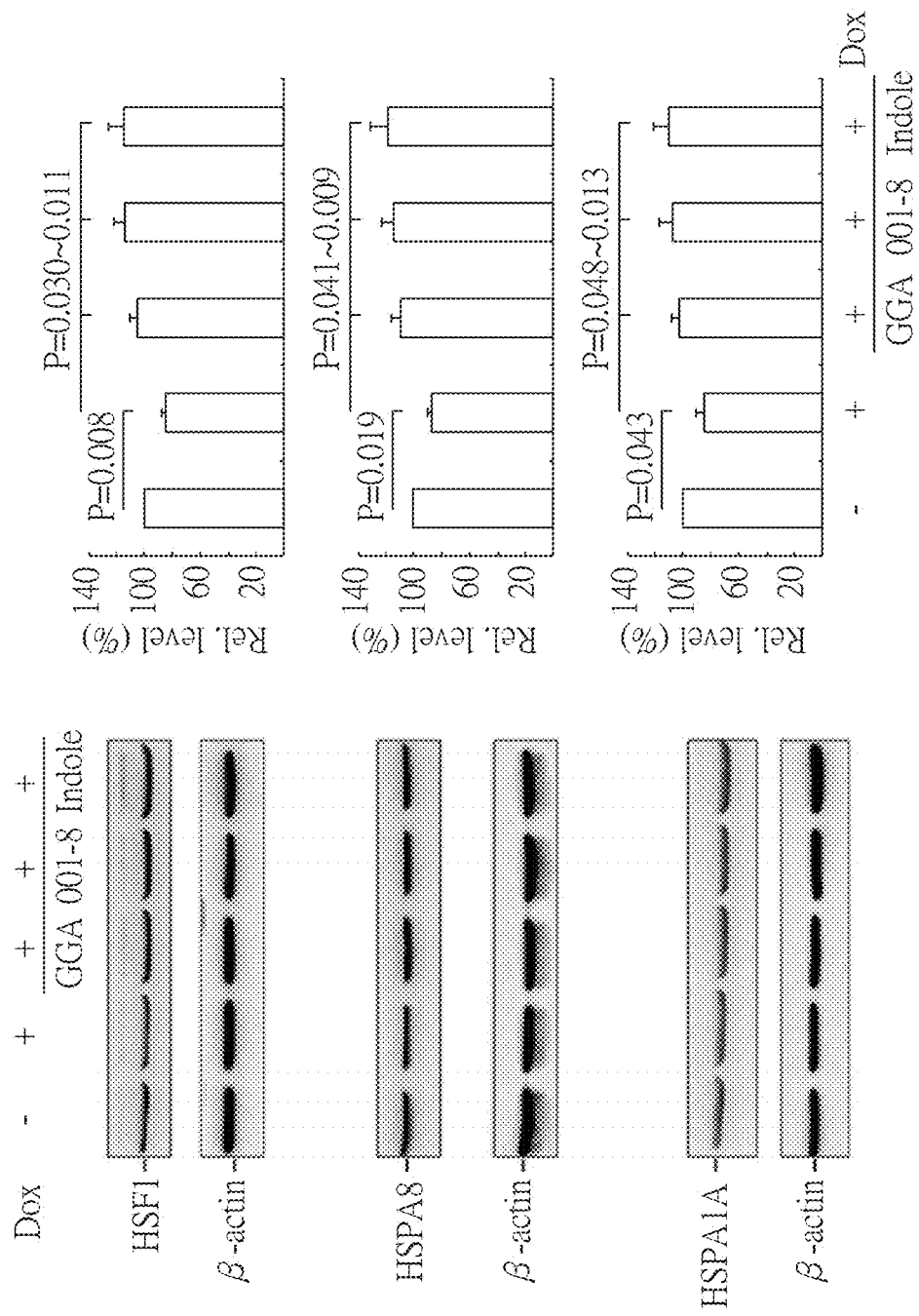
FIG. 5 shows a result of Western blot analysis of 293 ATXN3/$Q_{75}$ cells after treatment with the indole-based compounds according to one preferred embodiment of the present invention.

To examine if indole and NC001-8 also up-regulated HSF1 and chaperone expression in ATXN3/$Q_{75}$ 293 cells, we compared the expression levels of HSF1, HSPA8 and HSPA1A between with and without indole/NC001-8 and/or Dox treatment. As shown in FIG. 5, induced expression of ATXN3/$Q_{75}$ (+Dox) for 6 days attenuated the expression of HSF1 (85%, P=0.008), HSPA8 (86%, P=0.019) and HSPA1A (86%, P=0.043). This reduction can be rescued by the addition of GGA, indole or NC001-8 (100 nM), with significantly increased HSF1 (105%~115%, P=0.030~0.011), HSPA8 (109%~118%, P=0.041~0.009) and HSPA1A (104%~110%, P=0.048~0.013) expression. These findings indicated that in addition to GGA, indole and NC001-8 up-regulated HSF1 and chaperon expression to reduce ATXN3/$Q_{75}$ aggregation in cell model.

[Indole and Derivatives Enhanced Autophagy Activity on 293 ATXN3/$Q_{75}$ Cell Model]

Figure 6:
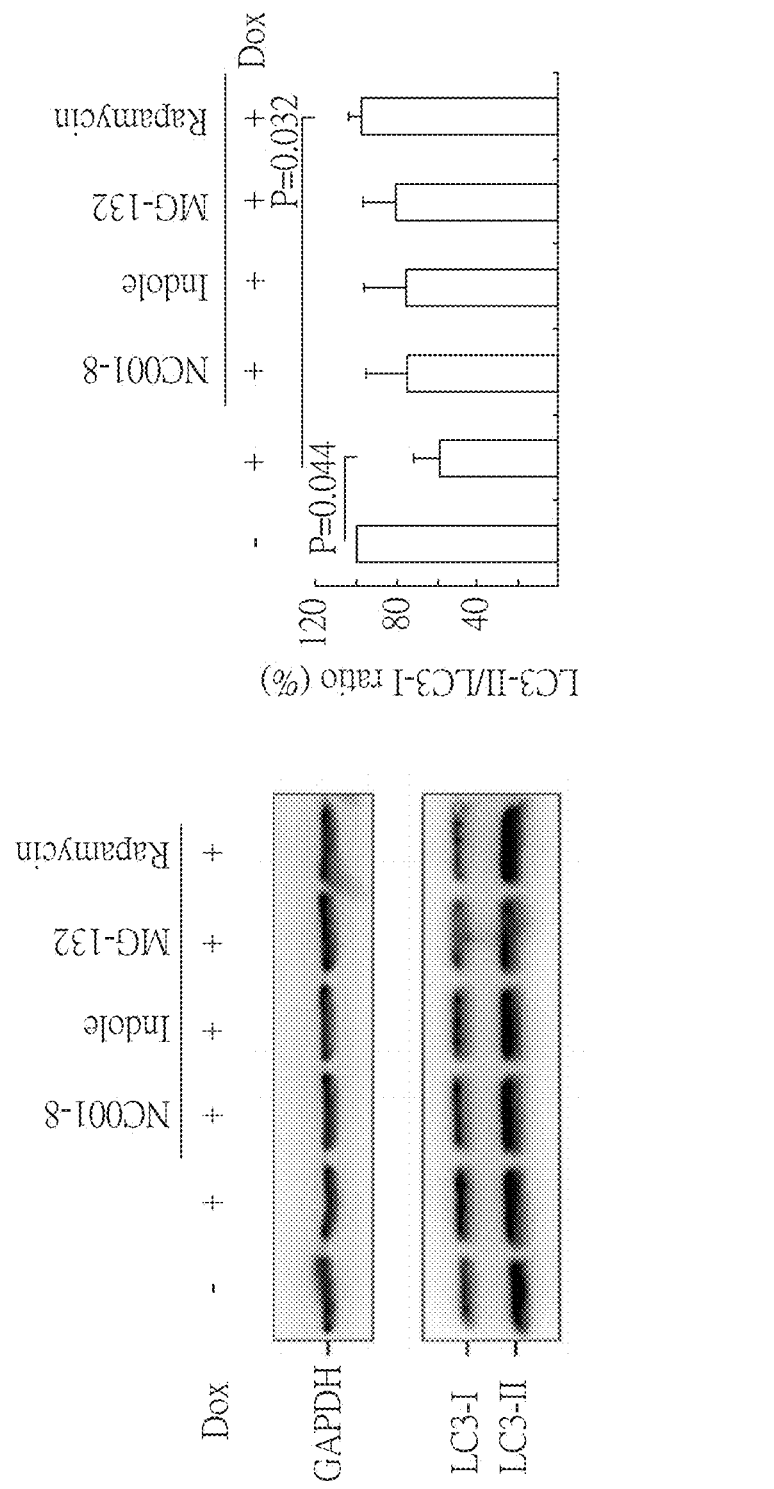
FIG. 6 shows a result presenting the LC3-II/LC3-I ratio in 293 ATXN3/$Q_{75}$ cells after treatment with the indole-based compounds according to one preferred embodiment of the present invention.

To examine if indole and NC001-8 also induced autophagy in ATXN3/$Q_{75}$ 293 cells, we compared the expression levels of lipid phosphatidylethanolamine (PE)-conjugated LC3-II and cytosolic LC3-I between with and without indole/NC001-8 and/or Dox treatment, as LC3-II is the only known protein that specifically associates with autophagosomes and not with other vesicular structures. As shown in FIG. 6, induced expression of ATXN3/$Q_{75}$ (+Dox) for 6 days attenuated the LC3-II/LC34 ratio (59%, P=0.044). This reduction can be rescued by the addition of indole, NC001-8, MG-132 (100 nM) or rapamycin (200 nM), with notably (indole, NC001-8 and MG-132: 75%~81%, P=0.215~0.412) or significantly (rapamycin: 98%, P=0.032) increased LC3-II/LC34 ratio. These findings indicated that indole and NC001-8 enhanced autophagy activity on 293 ATXN3/$Q_{75}$ cell model.

[Indole and Derivatives Reduced Reactive Oxygen Species on 293 ATXN3/$Q_{75}$ Cell Model]

Figures 7A, 7B:
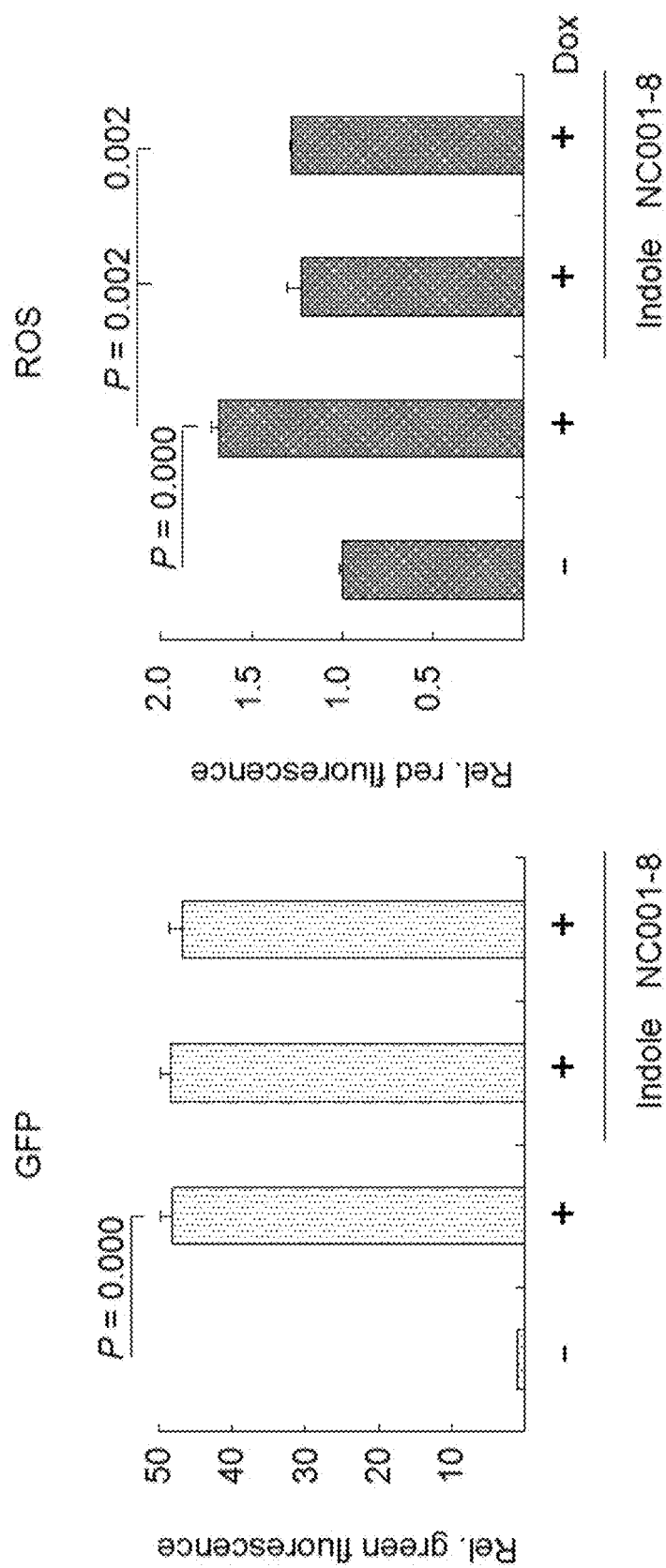
FIG. 7A shows green fluorescence level of 293 ATXN3/$Q_{75}$-GFP cells induced with doxycycline after treatment with the indole-based compounds according to one preferred embodiment of the present invention.
FIG. 7B shows red fluorescence (ROS) level of 293 ATXN3/$Q_{75}$-GFP cells induced with doxycycline after treatment with the indole-based compounds according to one preferred embodiment of the present invention.

To examine if indole and NC001-8 reduced reactive oxygen species in ATXN3/$Q_{75}$ 293 cells, we compared the reactive oxygen species concentration between with and without indole/NC001-8 and/or Dox treatment. As shown in FIGS. 7A-7B, induced expression of ATXN3/$Q_{75}$ (+Dox) for 6 days increased the production of reactive oxygen species (168%, P=0.000). This induction can be rescued by the addition of indole and NC001-8, with significantly (168% down to 123-428%, P=0.002) decreased reactive oxygen species. The induced expression of ATXN3/$Q_{75}$-GFP by Dox treatment was similar within the three groups. These findings indicated that indole and NC001-8 reduced reactive oxygen species on 293 ATXN3/$Q_{75}$ cell model.

[SH-SY5Y Cells with Induced SCA17 TBP/$Q_{79}$-GFP Expression and Neuronal Phenotype]

Figure 8A:
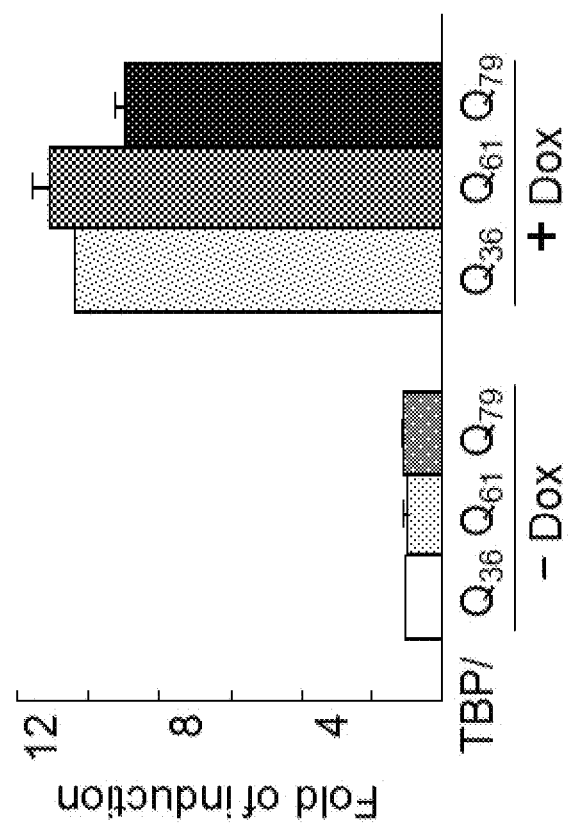
FIG. 8A shows real time PCR quantification of SH-SY5Y cells with induced SCA17 TBP/$Q_{36\sim79}$-GFP expression according to one preferred embodiment of the present invention.
Figure 8B:
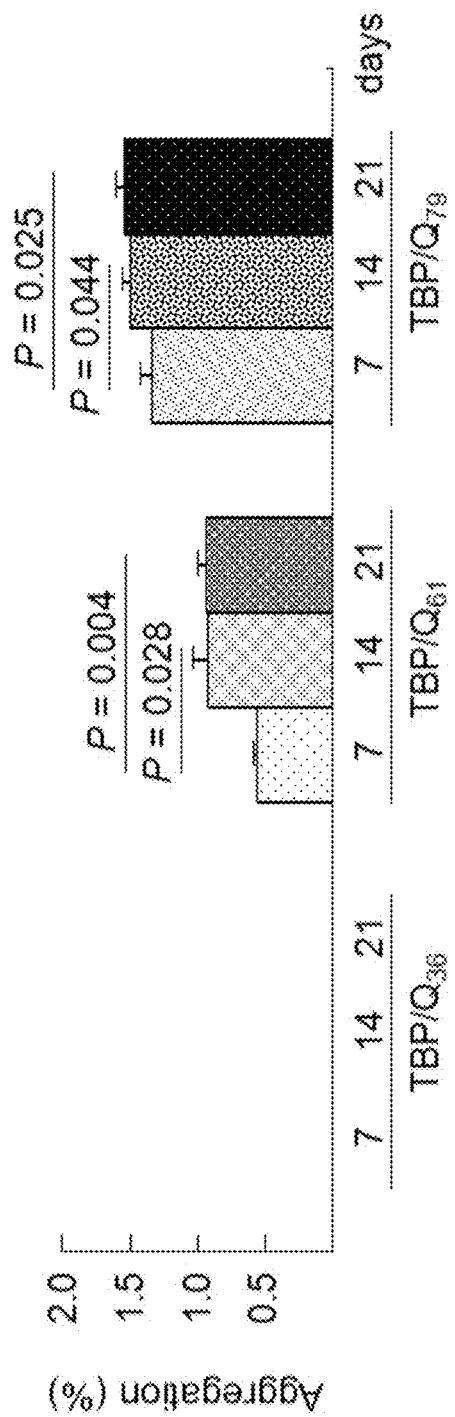
FIG. 8B shows a result of aggregation analysis from microscopic images of TBP/$Q_{36\sim79}$ SH-SY5Y cells induced differentiation with retinoic acid for 7~21 days according to one preferred embodiment of the present invention.
Figures 8C, 8D:
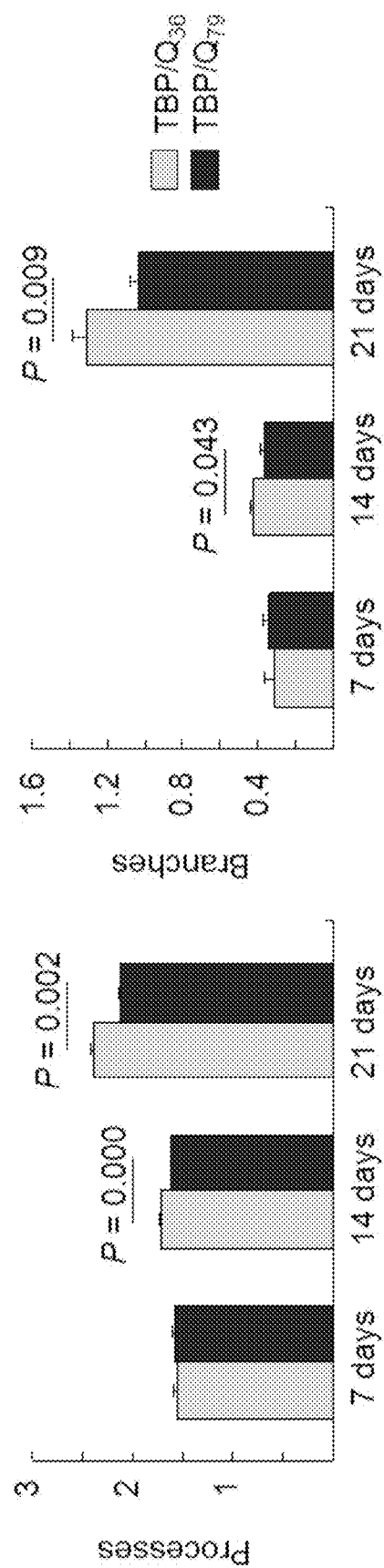
FIGS. 8C and 8D respectively show the neuronal processes and branches of TBP/$Q_{36\sim79}$ SH-SY5Y cells induced differentiation with retinoic acid for 7~21 days according to one preferred embodiment of the present invention.

As shown in FIG. 8A, real time PCR quantification of these TBP lines shows 9~11 times TBP expression after induction with doxycycline (+Dox) for 2 days. In immunoblot, TBP antibody detected 52~62 kDa TBP/$Q_{36\sim79}$-GFP protein, in addition to the endogenous 43 kDa TBP protein (figure not shown). When TBP/$Q_{36\sim79}$ SH-SY5Y cells were differentiated for 7 to 21 days using retinoic acid, a Q length- and expression time-dependent aggregate formation was seen in 1~2% TBP/$Q_{61\sim79}$-GFP cells, whereas no aggregate was seen in TBP/$Q_{36}$-GFP cells (FIG. 8B). When neuronal phenotype was examined after 7~21 days of differentiation, significant less process and branch in TBP/$Q_{79}$-GFP cells was observed at 2~3 weeks of differentiation compared to TBP/$Q_{36}$-GFP cells (P=0.000~0.002 for process; P=0.043~0.009 for branch) (FIGS. 8C-8D).

[Indole and Derivatives Reduced TBP/$Q_{79}$ Aggregation on SH-SY5Y Cell Model]

Figure 9A:
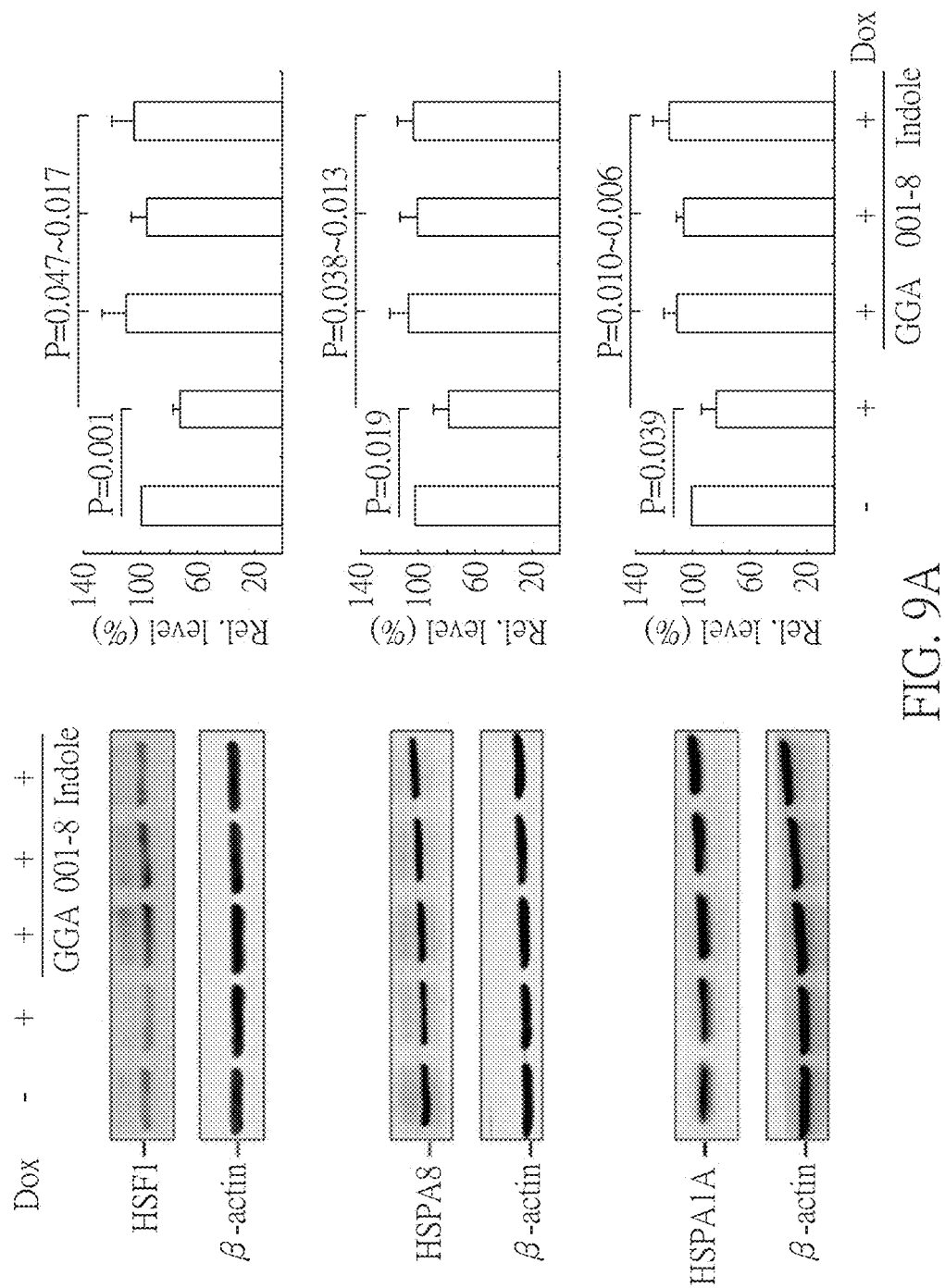
FIG. 9A shows a result of Western blot analysis of SH-SY5Y TBP cells after treatment with the indole-based compounds according to one preferred embodiment of the present invention.
Figure 9B:
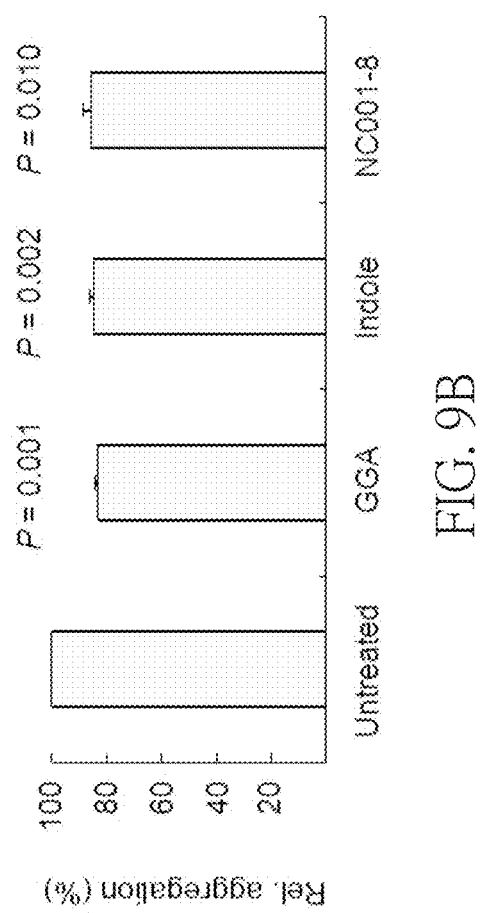
FIG. 9B shows a result of polyQ aggregation analysis of SH-SY5Y TBP cells after treatment with the indole-based compounds according to one preferred embodiment of the present invention.

To test the aggregation reduction potential of indole and NC001-8 in neuronal cells, we constructed Flp-In SH-SY5Y SCA17 cells with N-terminal TBP/$Q_{36-79}$-GFP expression in an inducible fashion and used to examine if indole and NC001-8 up-regulate HSF1, HSPA8 and HSPA1A expression to reduce aggregation. As shown in FIG. 9A, induced expression of TBP/$Q_{79}$ for 6 days attenuated the expression of HSF1, HSPA8 and HSPA1A (72~84%, P=0.001~0.039). This reduction can be rescued by the addition of GGA, indole or NC001-8 (100 nM) (96% 117%, P=0.047~0.006). The treatment of GGA, indole and NC001-8 leaded to 17%~14% of aggregation reduction (P=0.001~0.010) in TBP/$Q_{79}$ expressed differentiated neuronal cells (FIG. 9B). These findings indicated that indole and NC001-8 up-regulated HSF1 and chaperon expression to reduce TBP/$Q_{79}$ aggregation in differentiated neuronal cell model.

[Indole and Derivatives Promoted Purkinje Cell Neurite Outgrowth and Reduced Aggregation on SCA17 Mouse Primary and Slice Cultures]

Figure 10E:
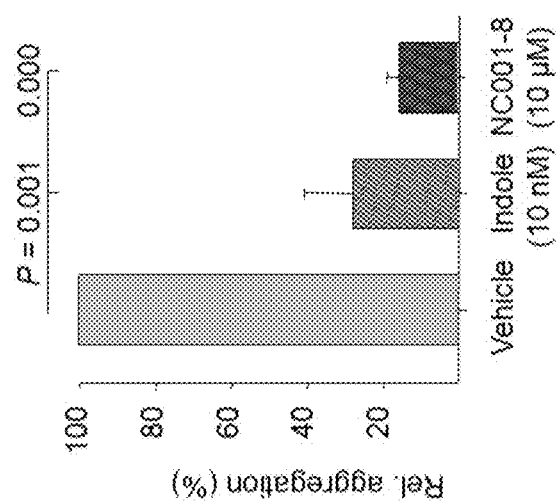
FIG. 10E shows a result of aggregation analysis of SCA17 mouse cerebellar slice culture after indole and NC001-8 treatments according to one preferred embodiment of the present invention.

To further confirm neuroprotective potential of the indole compounds, we applied indole and NC001-8 to the SCA17 mouse cerebellar primary and slice cultures, respectively. As shown in FIGS. 10A-10D, with 10~100 nM of compound concentration, significantly (indole: 134%~149%, P=0.016~0.002) or notably (NC001-8: 114%~119%, P>0.05) increased Purkinje cell neurite outgrowth were observed. Both compounds at concentrations 1~100 nM significantly reduced the Purkinje cell aggregation on the primary culture (indole: 86%~53%, P=0.039~0.001; NC001-8: 68%~60%, P=0.042~0.016). On SCA17 mouse cerebellar slice culture, while indole at 10 nM could significantly reduce the Purkinje cell aggregation (28%, P=0.001), one thousand folds of NC001-8 (10 μM) would be required to obtain a significant reduction of the aggregation (16%, P<0.001) (FIG. 10E). Thus indole worked more efficiently than NC001-8 in reducing the Purkinje cell aggregation on SCA17 mouse cerebellar slice culture.

Although the present invention has been explained in relation to its preferred embodiment, it is to be understood that many other possible modifications and variations can be made without departing from the spirit and scope of the invention as hereinafter claimed.

What is claimed is:

1. A method for treating an abnormal polyglutamine-mediated disease, comprising:
   administering a pharmaceutical composition to a subject in need, wherein the pharmaceutical composition comprises a compound selected from the group consisting of a compound of the following formula 1 and a compound of the following formula 2:

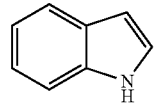

[Formula 1]

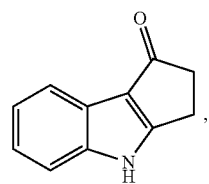

[Formula 2]

wherein the abnormal polyglutamine-mediated disease is spinocerebellar ataxia.

2. The method as claimed in claim 1, wherein a concentration of the compound is in a range from 1 nM to 50 μM in the pharmaceutical composition.

3. The method as claimed in claim 2, wherein a concentration of the compound is in a range from 10 nM to 10 μM in the pharmaceutical composition.

4. The method as claimed in claim 1, wherein the pharmaceutical composition decreases polyglutamine aggregation to treat the abnormal polyglutamine-mediated disease.

5. The method as claimed in claim 4, wherein the pharmaceutical composition reduces reactive oxygen species to decrease polyglutamine aggregation in the subject in need.

6. The method as claimed in claim 4, wherein the pharmaceutical composition enhances chaperone activity to decrease polyglutamine aggregation in the subject in need.

7. The method as claimed in claim 6, wherein the pharmaceutical composition activates heat shock transcription factor 1 (HSF1), heat shock cognate protein (HSPA8), or heat-inducible HSP70 chaperone (HSPA1A) to enhance chaperone activity in the subject in need.

8. The method as claimed in claim 4, wherein the pharmaceutical composition enhances autophagy activity to decrease polyglutamine aggregation in the subject in need.

9. The method as claimed in claim 8, wherein the pharmaceutical composition increases a ratio of LC3-II to LC3-I (LC3-II/LC3-I) to enhance the autophagy activity in the subject in need.

\* \* \* \* \*

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial sequence
<220> FEATURE:
<223> OTHER INFORMATION: Synthesized primer

<400> SEQUENCE: 1
attcagctaa gtatgcaagg tagttcca                                        28

<210> SEQ ID NO 2
<211> LENGTH: 30
<212> TYPE: DNA
<213> ORGANISM: Artificial sequence
<220> FEATURE:
<223> OTHER INFORMATION: Synthesized primer

<400> SEQUENCE: 2
catgccatgg catgttttt tccttctgtt                                       30
```